US006500940B1

(12) United States Patent
Verma et al.

(10) Patent No.: US 6,500,940 B1
(45) Date of Patent: Dec. 31, 2002

(54) LIFEGUARD (LFG) POLYNUCLEOTIDES AND POLYPEPTIDES AND METHODS OF USE THEREOF

(75) Inventors: Inder M. Verma, La Jolla, CA (US); Mark Schmitt, La Jolla, CA (US); Nikunj V. Somia, La Jolla, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 09/328,714

(22) Filed: Jun. 9, 1999

(51) Int. Cl.$^7$ .............................................. C07H 21/04
(52) U.S. Cl. ..................... 536/23.5; 536/24.1; 530/350; 435/320.1; 435/325; 435/252.3; 435/235
(58) Field of Search .......................... 514/44; 536/23.5, 536/24.1; 435/320.1, 69.1, 325, 252.3, 235; 530/350

(56) References Cited

FOREIGN PATENT DOCUMENTS

| WO | 9817687 | 4/1998 |
|---|---|---|
| WO | 9966041 | 12/1999 |

OTHER PUBLICATIONS

Liles et. al.; Accession No. 96343853, 1996.*
Voet et. al.; Biochemistry1978, Annu. Rev. Biochem. 47: 258.*
Rudinger, Characteristics of the amino acids as components of a peptide hormone sequence, 1976,Peptide Hormones: 5–6.*
Ngo et. al.; Computational Complexity, Protein Structure Prediction, and the Levinthal Paradox, 1994, The Protein Folding Problem and Teriary Structure Prediction: 491–495.*
Nagase et. al.; Prediction of the coding sequences of unidentified human genes. XIII. The complete sequences of 100 new cDNA clones from brain which code for large proteins in vitro, 1999, DNA RES 26: 63–70.*
Jacobs et. al.; GenBank v30928, 1998.*
Nagase, et al., *Homo sapiens mRNA for KIAA0950 protein, partial cds;* Database EMBL; Accession No.: AB023167; Apr. 9, 1999.
Somia, Nikunjv et al., *LFG: An anti–apoptotic gene that provides protection from Fas–mediated cell death.* Proc. of the Nat. Acad. of Sciences of U.S.; vol. 96:22: pps. 12667–12672 1999.
geneback locus S61973.
genebank locus CEF40F9.
genebank locus DRONMDA.
B. Schweitzer et al., "Neural Membrane Protein 35 (NMP35): A Novel Member of a Gene Family Which Is Highly Expressed in the Adult Nervous System,"*Mol. Cell Neurosci.,* 11, 260 (1998).
A. Pellicena–Palle et al., "The putative *Drosophila* NMDARA1 gene is located on the second chromosome and is ubiquitously expressed in embryogenesis," *Biochim. Biophys. Acta,* 1261, 301 (1995).
K.S. Khabar et al., "WEHI–13VAR: a stable and sensitive variant of WEHI 164 clone 13 fibrosarcoma for tumor necrosis factor bioassay," *Immunol. Lett.,* 46, 107 (1995).
S.R. Wiley et al., "Identification and Characterization of a New Member of the TNF Family that Induces Apoptosis," *Immunity,* 3, 673 (1995).
K.N. Kumar et al., "Cloning of cDNA for the glutamate–binding subunit of an NMDA receptor complex," *Nature,* 354, 70 (1991).

* cited by examiner

Primary Examiner—James Ketter
Assistant Examiner—Richard Schnizer
(74) Attorney, Agent, or Firm—Knobbe, Martens, Olson & Bear, LLP

(57) ABSTRACT

A substantially purified lifeguard (LFG) polypeptide is provided. The polypeptide includes an amino acid sequence as set forth in SEQ ID NO:2, or a conservative variant thereof. An isolated polynucleotide is provided that encodes an amino acid sequence as set forth in SEQ ID NO:2, or a conservative variant thereof. An antibody is provided that binds to a polypeptide having an amino acid sequence as set forth in SEQ ID NO:2. A method is provided for identifying a compound which affects a function a polypeptide as set forth in SEQ ID NO:2, or a conservative variant thereof, or affects the expression of a polynucleotide comprising a sequence as set forth in SEQ ID NO:1. A method is provided for treating a subject with a disorder associated with decreased or increased Fas-mediated cell death. A method is provided for treating a patient having or at risk of having a disorder associated with increased Fas-mediated cell death.

13 Claims, 7 Drawing Sheets

ATGACCCGGGGAAAGCTCTCCGTGGCTAACAAGGCCCCTGGGACCGAGGGGCAGCA
GCAGGTGCATGGCGAGAAGAAGGA
GGCTCCAGCAGTGCCCTCAGCCCCACCCTCCTATGAGGAAGCCACCTCTGGGGAGGG
GATGAAGGCAGGGGCCTTCCCCC
CAGCCCCCACAGCGGTGCCTCTCCACCCTAGCTGGGCCTATGTGGACCCCAgCAGCA
GCTCCAGCTATGACAACGGTTTC
CCACCGGAGACCATGAGCTCTTCACCACTTTCAGCTGGGATGACCAAGAAAGTTCGT
CGAGTCTTTGTCAGAAAGGTCTA
CACCATCCTGCTGATTCAACTGCTGGTGACCTTGGCTGTCGTGGCTCTCTTTACTTTC
TGTGACCCTTGTCAAGGACTAT
GTTCAGGCCAACCAGGCTGGTACTGGGCATCCTATGCTGTGTTCTTTGCAACCTACCT
GACCCTGGCTTGCTGTTCTGGA
CCCAGGAGGCATTTCCCCTGGAACCTGATTCTCCTGACCGTCTTTACCCTGTCCATGG
CCTACCTCACTGGGATGCTGTC
CAGCTACTACAACACCACCTCCGTGCTGCTGTGCCTGGGCATCACGGCCCTTGTCTG
CCTCTCAGTCACCGTCTTCAGCT
TCCAGACCAAGTTCGACTTCACCTCCTGCCAGGGCGTGCTCTTCGTGCTTCTCATGAC
TCTTTTCTTCAGCGGACTCATC
CTGGCCATCCTCCTACCCTTCCAATATGTGCCCTGGCTCCATGCAGTTTATGCAGCAC
TGGGAGCGGGTGTATTTACATT
GTTCCTGGCACTTGACACCCAGTTGCTGATGGGTAACCGACGCCACTCGCTGAGCCC
TGAGGAGTATATTTTTGGAGCCC
TCAACATTTACCTAGACATCATCTATATCTTCACCTTCTTCCTGCAGCTTTTTGGCACT
AACCGAGAATGA

The coding sequence is translated into proteins as:

MTRGKLSVANKAPGTEGQQQVHGEKKEAPAVPSAPPSYEEATSGEGMKAGAFPPAPTA
VPLHPSWAYVDPSSSSYDNGF
PPETMSSSPLSAGMTKKVRRVFVRKVYTILLIQLLVTLAVVALFTFCDPCQGLCSGQPGW
YWASYAVFFATYLTLACCSG
PRRHFPWNLILLTVFTLSMAYLTGMLSSYYNTTSVLLCLGITALVCLSVTVFSFQTKFDFT
SCQGVLFVLLMTLFFSGLI
LAILLPFQYVPWLHAVYAALGAGVFTLFLALDTQLLMGNRRHSLSPEEYIFGALNIYLDII
YIFTFFLQLFGTNREZ

*FIG. 3*

LIFEGUARD (LFG) POLYNUCLEOTIDES AND POLYPEPTIDES AND METHODS OF USE THEREOF

FIELD OF THE INVENTION

This invention relates generally to the field of apoptosis, and more specifically to the inhibition of Fas-mediated apoptosis.

BACKGROUND OF THE INVENTION

Necrosis and apoptosis are two basic processes by which cells may die. In necrosis, cell death usually is a result of cell injury. The cells tend to swell and lyse, and the cell contents ultimately spill into the extracellular space. By contrast, apoptosis is a mode of cell death in which single cells are deleted in the midst of living tissues. Apoptosis, or programmed cell death, is utilized in a number of biological processes that include modeling the embryo, regulating the immune system, and tumor regression (M. D. Jacobson et al., *Cell*, 347, 1997; A. Winoto, *Curr. Opin. Immunol.*, 9, 365, 1997; G. Evan, et al., *Science*, 281, 1998; H. Arai et al., *Proc. Natl. Acad. Sci. USA*, 94, 13862, 1997). For example, apoptosis accounts for most of the programmed cell death in tissue remodeling and for the cell loss that accompanies atrophy of adult tissues following withdrawal of endocrine and other growth stimuli. In addition, apoptosis is believed to be responsible for the physiologic death of cells in the course of normal tissue turnover (i.e., tissue homeostasis) (Kerr, J. F.,et al, 1972. *Br. J. Cancer* 26:239–257; Wyllie, A. H., et al. 1980. *Int. Rev. Cytol.* 68:251–306). As an example, apoptosis is observed in the immune system as the process by which B and T lymphocytes are removed when they fail to recognize a foreign antigen or when they are self-reactive.

The deregulation of programmed cell death may result in a disease state. Dysfunction of the apoptotic system has been implicated in oncogenesis, development of autoimmunity and degenerative diseases. Degenerative diseases which result from excessive cell death include degenerative neurological diseases, such as Alzheimer's disease and Parkinson's disease which are associated with the death of particular subsets of neurons. The inopportune death of T cells in AIDS may be associated with physiological cell death. Physiological cell death may also be associated with transplant rejection. Diseases due to increased cellular proliferation are also possible due to deregulation of the apoptotic mechanism and include autoimmune diseases in which self-reactive B and T cells are allowed to persist. The term "physiological cell death" is used here to describe cell death that occurs by a mechanism that exists in the mammal to kill its own cells and includes apoptosis and programmed death as synonymous terms.

An imbalance of the cell proliferation and cell degeneration processes also may lead to development of neoplasias in cells deregulated for the control of apoptosis. As a protective mechanism against cancer, tumor necrosis factor can trigger apoptosis in transformed host cells. An important example of the type of cancers which develop when cell proliferation exceeds the normal balance, is human follicular lymphoma. As with other malignancies where the development of neoplasia is related to an oncogene, follicular lymphoma is characterized by a chromosomal breakpoint. The rearrangement in follicular lymphoma is the most common chromosomal translocation in human lymphoid malignancies, the t(14;18)(q32;q21) translocation, which is known to inhibit programmed cell death in B cells. The bcl-2 gene is translocated and deregulated in follicular lymphoma.

Intense studies of apoptosis in the last decade have identified membrane bound receptors, and their cognate ligands that together begin a program that ultimately leads to cell death (A. Ashkenazi, *Science*, 281, 1305, 1998). One of the most characterized receptors is Fas (also called CD95 or Apo-1) belonging to the tumor necrosis factor receptor (TNFR) superfamily (N. Itoh et al., *Cell*, 66, 233 1991; A. Oehm et al., *J. Biol. Chem.*, 267, 10709, 1992). Binding of soluble or cell-surface expressed CD95 ligand to CD95 leads to oligomerization of the receptor and the subsequent the transmission of the apoptosis signal. Fas has three cysteine—rich extracellular domains and an intracellular death domain (DD) required for signaling (N. Itoh et al., *J. Biol. Chem.*, 268, 10932, 1993). Ligation of the receptor by its cognate ligand, FasL (T. Suda et al., *Cell*, 75, 1169, 1993), or an agonistic antibody (S. Yonehara et al., *J. Exp. Med.*, 169, 1747, 1989), leads to the recruitment of a cytoplasmic adapter molecule FADD (also called MORT-1), mediated by a DD in FADD and the DD of Fas (A. M. Chinnaiyan et al., *Cell*, 81, 505, 1995; Boldin et al., *J. Biol. Chem.*, 270, 7795, 1995). Additionally, FADD contains a death effector domain (DED) that recruits the protease caspase-8 (also called FLICE, MACH and Mch5) to the signaling complex M. Muzio et al., *Cell*, 85, 817, 1996; M. P. Boldin et al., *Cell*, 85, 803, 1996; S. M. Srinivasula et al., *Proc. Natl. Acad. Sci. USA*, 93, 14486, 1996). This zymogen, through proximity with other caspase-8 molecules, is cleaved rendering it fully active, thus beginning a protease cascade that leads to cell death (M. Muzio et al., *J. Biol. Chem.*, 273, 2926, 1998). A counterpoint to this activation is inhibition of apoptosis.

SUMMARY OF THE INVENTION

Apoptosis plays an important role in the homeostasis and development of all tissues within an organism. The present invention relates to a novel apoptotic-associated polypeptide Lifeguard (LFG), and to the use of LFG antibodies, nucleic acid sequences, and amino acid sequences in the study, and treatment of apoptosis-associated disorders.

A substantially purified lifeguard (LFG) polypeptide is provided. The polypeptide includes an amino acid sequence as set forth in SEQ ID NO:2, or a conservative variant thereof.

An isolated polynucleotide is provided that encodes an amino acid sequence as set forth in SEQ ID NO:2, or a conservative variant thereof. An isolated polynucleotide is provided selected from the group consisting of SEQ ID NO:1, where T can also be a U, SEQ ID NO:1, a nucleic acid sequence complementary to SEQ ID NO:1, and fragments of SEQ ID NO:1 that are at least 15 bases in length and that hybridize under highly stringent conditions to DNA which encodes a polypeptide as set forth in SEQ ID NO:2.

An antibody is provided that binds to a polypeptide having an amino acid sequence as set forth in SEQ ID NO:2.

A method is provided for identifying a compound which affects a function a polypeptide as set forth in SEQ ID NO:2, or a conservative variant thereof, or affects the expression of a polynucleotide including a sequence as set forth in SEQ ID NO:1. The method includes incubating the compound and a cell expressing the polypeptide under conditions sufficient to allow the compound to interact with the cell, determining the effect of the compound on Fas-mediated cell death, and comparing Fas-mediated cell death of the cell contacted with the compound with Fas-mediated cell death of a cell not contacted with the compound.

A method is provided for treating a subject with a disorder associated with decreased Fas-mediated cell death, including administering to the subject a therapeutically effective amount of a compound that inhibits LFG function or expression. A method is also provided for treating a subject with a disorder associated with increased Fas-mediated cell, including administering to the subject a therapeutically effective of a compound that augments LFG function or expression.

A method is provided for treating a patient having or at risk of having a disorder associated with increased Fas-mediated cell death, including introducing into a cell of a patient having a disorder associated with Fas-mediated cell death a polynucleotide sequence encoding a SEQ ID NO:2 operatively linked to a promoter, thereby inhibiting Fas-mediated cell death.

A pharmaceutical composition is provided that includes a therapeutically effective amount of a substantially pure LFG polypeptide as set forth as SEQ ID NO:2, or a conservative variant thereof, and a pharmaceutically acceptable carrier.

A kit for is provided for detecting the presence of LFG in a sample. The kit includes a carrier means being compartmentalized to receive therein one or more containers comprising a container containing an antibody which specifically binds to LFG. A kit is also provided that is useful for the detection of a target LFG nucleic acid sequence. The kit includes a carrier means being compartmentalized to receive therein one or more containers including a container containing oligonucleotides which hybridize to LFG nucleic acid sequences.

A transgenic nonhuman animal is provided wherein the transgenic animal has a phenotype characterized by expression of LFG, otherwise not naturally occurring in the animal, the phenotype being conferred by a transgene contained in the somatic and germ cells of the animal. The transgene includes a nucleic acid sequence which encodes SEQ ID NO:2. In one embodiment, transgenic animals having gene knockouts in which the target gene has been rendered nonfunctional by an insertion targeted to the gene to be rendered non-functional by homologous recombination are provided.

BRIEF DESCRIPTION OF THE DRAWINGS

FIG. 1 is the composition of the 316 amino acid LFG protein (SEQ ID NO:2) and a comparison of sequences.

FIG. 3 shows the nucleotide (SEQ ID NO:1) and amino acid (SEQ ID NO:2) sequences of LFG.

DETAILED DESCRIPTION OF THE INVENTION

Figure 1A:
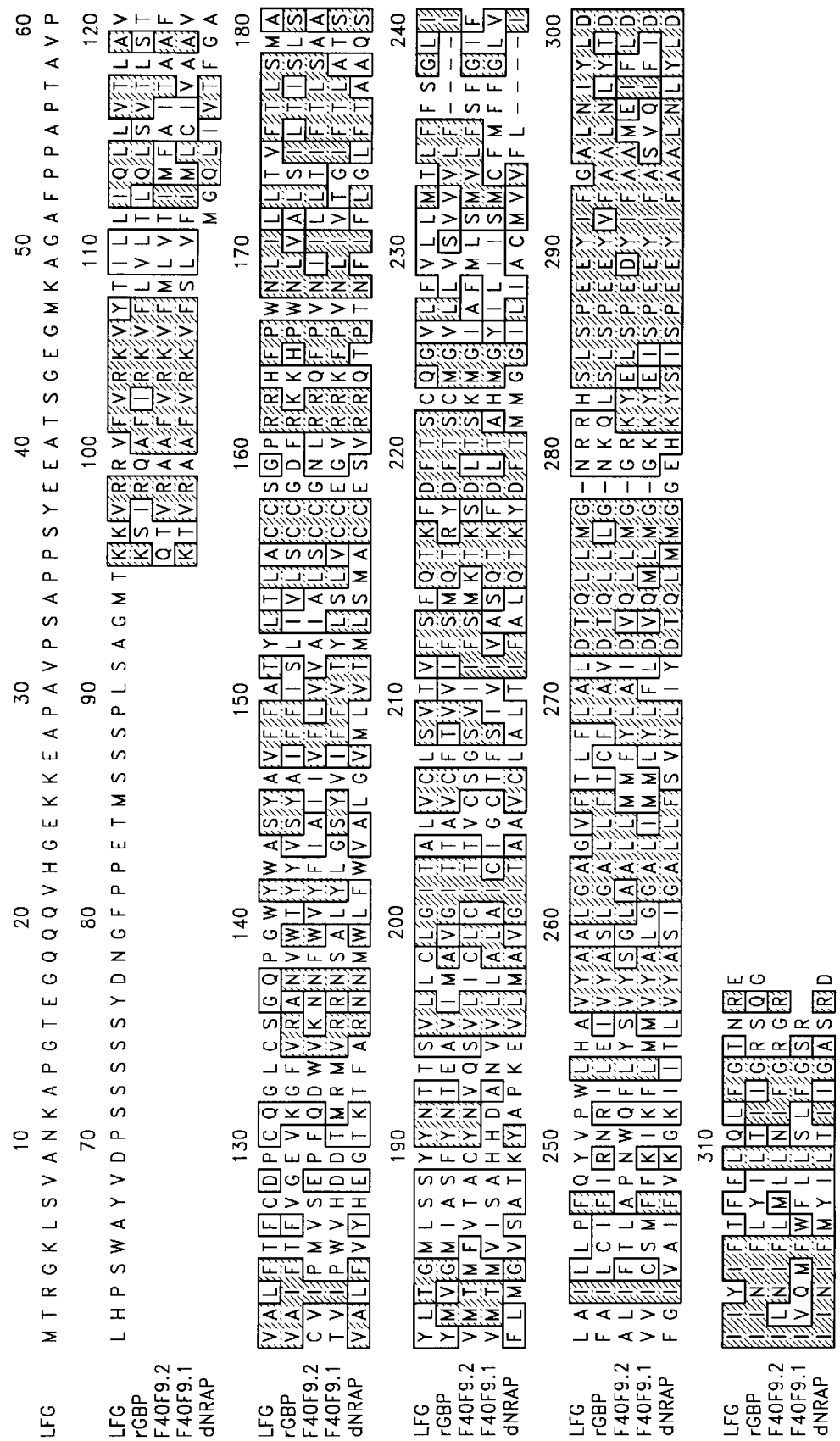
FIG. 1A illustrates sequence homology for the most significant parts of the 516 amino acid rat glutamate binding protein (rGBP; genebank locus S61973 (herein incorporated by reference; amino acids 129–345 shown as SEQ ID NO:3); C. elegans open reading frame (genebank locus CEF40F9, herein incorporated by reference) of the F40F9.2 (244 amino acids total, 25–244 shown as SEQ ID NO:4) and F40F9.1 (295 amino acids total, 77–295 shown as SEQ ID NO:5) and a 203 amino acid Drosophila NMDA receptor associated protein (genebank locus DRONMDA, herein incorporated by reference; 1–203 shown as SEQ ID NO:6). BLAST homology searches reveal highest homologies in the C-terminus of LFG (from amino acid 141). Identity scores are 50% for rGBP, 46% and 42% for F40F9.2 and F40F9.1 respectively, and 42% for dNRAP.

The present invention relates to lifeguard (LFG) polypeptide and to the use of lifeguard (LFG) antibodies, nucleic acid sequences, and amino acid sequences in the study and treatment of apoptosis-associated disorders. Apoptosis plays an important role in the homeostasis and development of all tissues within an organism.

POLYNUCLEOTIDES AND POLYPEPTIDES

In one embodiment, the invention provides substantially purified lifeguard (LFG) polypeptide. Preferably, LFG has an amino acid sequence set forth in SEQ ID NO:2. The term "substantially purified" as used herein refers to a polypeptide which is substantially free of other proteins, lipids, carbohydrates or other materials with which it is naturally associated. One skilled in the art can purify LFG using standard techniques for protein purification. The substantially pure polypeptide will yield a single major band on a non-reducing polyacrylamide gel. The purity of the LFG polypeptide can also be determined by amino-terminal amino acid sequence analysis.

Minor modifications of the LFG primary amino acid sequences may result in proteins which have substantially equivalent activity as compared to the unmodified counterpart polypeptide described herein. Such modifications may be deliberate, as by site-directed mutagenesis, or may be spontaneous. All of the polypeptides produced by these modifications are included herein as long as the biological activity of the LFG still exists. Further, deletion of one or more amino acids can also result in a modification of the structure of the resultant molecule without significantly altering its activity. Deletion can lead to the development of a smaller active molecule which could have broader utility. For example, it may be possible to remove amino or carboxy terminal amino acids without altering LFG activity.

The invention includes functional LFG polypeptides as well as functional fragments thereof. As used herein, the term "functional polypeptide" refers to a polypeptide which possesses biological function or activity which is identified through a defined functional assay and which is associated with a particular biologic, morphologic, or phenotypic alteration in the cell. The term "functional fragments of LFG polypeptide," refers to all fragments of a LFG polypeptide that retain a LFG activity, e.g., the ability to protect a cell from apoptosis. Biologically functional fragments, for example, can vary in size from a polypeptide fragment as small as an epitope capable of binding an antibody molecule to a large polypeptide capable of participating in the characteristic induction or programming of phenotypic changes within a cell. For example, functional fragments of LFG can still protect a cell from apoptosis.

LFG polypeptide includes amino acid sequences substantially the same as the sequence set forth in SEQ ID NO:2. The term "substantially the same" refers to amino acid sequences that retain the activity of LFG as described herein, e.g., the ability to protect a cell from Fas-mediated apoptosis. The LFG polypeptides of the invention include conservative variations of the polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The polypeptides of the invention also include dominant negative forms of the LFG polypeptide which do not have the biological activity of LFG. A "dominant negative form" of LFG is a polypeptide that is structurally similar to LFG but does not have wild-type LFG function. For example, a dominant-negative LFG polypeptide may interfere with wild-type LFG function by binding to, or otherwise sequestering, regulating agents, such as upstream or downstream components, that normally interact functionally with the LFG polypeptide.

The invention provides polynucleotides encoding the LFG protein. These polynucleotides include DNA, cDNA and RNA sequences which encode LFG. It is understood that all polynucleotides encoding LFG are also included herein, as long as they encode a polypeptide with LFG activity. Such polynucleotides include naturally occurring, synthetic, and intentionally manipulated polynucleotides. For example, LFG polynucleotide may be subjected to site-directed mutagenesis. The polynucleotide sequence for LFG also includes antisense sequences, and sequences encoding dominant negative forms of LFG. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of LFG polypeptide encoded by the nucleotide sequence is functionally unchanged.

Specifically disclosed herein is a polynucleotide sequence containing the LFG gene which encodes the amino acid sequence of SEQ ID NO:2. An exemplary LFG nucleotide sequence is set forth in SEQ ID NO:1. The term "polynucleotide" or "nucleic acid sequence" refers to a polymeric form of nucleotides at least 10 bases in length. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g. a cDNA) independent of other sequences. The nucleotides of the invention can be ribonucleotides, deoxyribonucleotides, or modified forms of either nucleotide. The term includes single and double forms of DNA.

The polynucleotide encoding LFG includes SEQ ID NO:1, polynucleotides encoding dominant negative forms of LFG, and nucleic acid sequences complementary to SEQ ID NO:1. A complementary sequence may include an antisense nucleotide. When the sequence is RNA, the deoxynucleotides A, G, C, and T of SEQ ID NO:1 are replaced by ribonucleotides A, G, C, and U, respectively. Also included in the invention are fragments of the above-described nucleic acid sequences that are and are at least 15 bases in length, which is sufficient to permit the fragment to selectively hybridize to DNA that encodes the protein of SEQ ID NO:2 under physiological conditions or a close family member of LFG. The term "selectively hybridize" refers to hybridization under moderately or highly stringent conditions which excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

The nucleotide sequence encoding the LFG polypeptide of the invention includes the disclosed sequence and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences encoding LFG can be expressed in vitro by DNA transfer into a suitable host cell. "Host cells" are cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the LFG polynucleotide sequences may be inserted into an expression vector. The term "expression vector" refers to a plasmid, virus or other vehicle known in the art that has been manipulated by insertion or incorporation of the LFG genetic sequences. Polynucleotide sequence which encode LFG can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to included, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., 1987, Methods in Enzymology 153:516–544). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

In the present invention, the polynucleotide encoding LFG may be inserted into an expression vector which contains a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., 1987, Gene, 56:125), the pMSXND expression vector for expression in mammalian cells (Lee and Nathans, 1988, *J. Biol. Chem.*, 263:3521) and baculovirus-derived vectors for expression in insect cells. The DNA segment can be present in the vector operably linked to regulatory elements, for example, a promoter (e.g., T7, metallothionein I, or polyhedron promoters).

Polynucleotide sequences encoding LFG can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

By "transformation" is meant a genetic change induce in a cell following incorporation of new DNA (i.e. DNA exogenous to the cell). Where the cell is a mammalian cell, the genetic change is generally achieved by introduction of the DNA into the genome of the cell (i.e. stable).

By "transformed cell" is meant a cell into which (or into an ancestor of which) has been introduced, by means of recombinant DNA techniques, a DNA molecule encoding LFG. Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the LFG polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

ANTIBODIES

The LFG polypeptides of the invention can be used to produce antibodies which are immunoreactive or bind to epitopes of the LFG polypeptides. Antibodies which consist essentially of pooled monoclonal antibodies with different epitopic specificities, as well as distinct monoclonal antibody preparations are provided.

The preparation of polyclonal antibodies is well-known to those skilled in the art. See, for example, Green et al., Production of Polyclonal Antisera, in: *Immunochemical Protocols* (Manson, ed.), pages 1–5 (Humana Press 1992); Coligan et al., Production of Polyclonal Antisera in Rabbits, Rats, Mice and Hamsters, in: *Current Protocols in Immunology*, section 2.4.1 (1992), which are hereby incorporated by reference.

The preparation of monoclonal antibodies likewise is conventional. See, for example, Kohler & Milstein, 1975, Nature 256:495; Coligan et al., sections 2.5.1–2.6.7; and Harlow et al., in: *Antibodies: a Laboratory Manual*, page 726 (Cold Spring Harbor Pub. 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., Purification of Immunoglobulin G (IgG), in: *Methods in Molecular Biology*, Vol. 10, pages 79–104 (Humana Press 1992).

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for antibodies disclosed herein are also part of the present invention. For example, antibodies of the present invention may also be derived from subhuman primate antibody. General techniques for raising therapeutically useful antibodies in baboons can be found, for example, in Goldenberg et al., International Patent Publication WO 91/11465 (1991) and Losman et al., 1990, *Int. J. Cancer* 46:310, which are hereby incorporated by reference.

Alternatively, a therapeutically useful anti-LFG antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., 1989, Proc. Nat'l Acad. Sci. USA 86:3833, which is hereby incorporated in its entirety by reference. Techniques for producing humanized monoclonal antibodies are described, for example, by Jones et al., 1986, Nature 321:522; Riechmann et al., 1988, Nature 332:323; Verhoeyen et al., 1988, Science 239:1534; Carter et al., 1992, Proc. Nat'l Acad. Sci. USA 89:4285; Sandhu, 1992, Crit. Rev. Biotech. 12:437; and Singer et al., 1993, J. Immunol. 150:2844, which are hereby incorporated by reference.

Antibodies of the invention also may be derived from human antibody fragments isolated from a combinatorial immunoglobulin library. See, for example, Barbas et al., 1991, in: *Methods: a Companion to Methods in Enzymology*, Vol. 2, page 119; Winter et al., 1994, Ann. Rev. Immunol. 12:433, which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., 1994, Nature Genet. 7:13; Lonberg et al., 1994, Nature 368:856; and Taylor et al., 1994, Int. Immunol. 6:579, which are hereby incorporated by reference.

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, New York (1988), incorporated herein by reference). As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments of the present invention can be prepared by proteolytic hydrolysis of the antibody or by expression in E. coli of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. No. 4,036,945 and U.S. Pat. No. 4,331,647, and references contained therein. These patents are hereby incorporated in their entireties by reference. See also Nisonhoff et al., 1960, Arch. Biochem. Biophys. 89:230, Porter, 1959, Biochem. J. 73:119; Edelman et al., 1967, *Methods in Enzymology*, Vol. 1, page 422 (Academic Press); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., 1972, Proc. Nat'l Acad. Sci. USA 69:2659. Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow et al., 1991, *Methods: a Companion to Methods in Enzymology*, Vol. 2, page 97; Bird et al., 1988, Science 242:423–426; Ladner et al., U.S. Pat. No. 4,946,778; Pack et al., 1993, Bio/Technology 11:1271–77; and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: a Companion to Methods in Enzymology*, Vol. 2, page 106 (1991).

Antibodies which bind to the LFG polypeptide of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

METHOD FOR IDENTIFYING COMPOUNDS WHICH AFFECT lifeguard (LFG)

The invention provides a method for identifying a compound which can modulate LFG activity. The method includes incubating the compound and a cell expressing LFG, under conditions sufficient to allow the compound of interest to interact with the cell, and measuring the effect of the compound on the activity of LFG. In one embodiment, the activity of LFG in the sample is assessed by measuring Fas-mediated cell death. The activity of LFG in the sample can then be compared to the lifeguard LFG activity of a control sample not incubated with the compound. The effect of the compound on lifeguard (LFG) can be measured by assessing the expression of lifeguard (LFG) by methods well known in the art (e.g., Northern blots). Alternatively, the effect of the compound on the activity of lifeguard (LFG) can be assessed. For example, in order to determine the effect of the compound on apoptosis can be measured (see below).The compounds which affects LFG include peptides, polypeptides, chemical compounds and biological agents.

"Incubating" includes conditions which allow contact between the test compound and the cell expressing LFG. "Contacting" includes in solution and solid phase. The test compound may also be a combinatorial library for screening a plurality of compounds. Compounds identified in the method of the invention can be further evaluated, detected, cloned, sequenced, and the like, either in solution of after binding to a solid support, by any method usually applied to the detection of a specific DNA sequence, such as PCR, oligomer restriction (Saiki et al.,1985, Bio/Technology, 3:1008–1012), allele-specific oligonucleotide (ASO) probe analysis (Conner et al.,1983, Proc. Natl. Acad. Sci. USA, 80:278), oligonucleotide ligation assays (OLAs) (Landegren et al., 1988, Science, 241:1077), and the like. Molecular techniques for DNA analysis have been reviewed (Landegren et al., 1988, Science, 242:229–237).

A variety of other agents may be included in the screening assay. These include agents like salts, neutral proteins, e.g., albumin, detergents, etc that are used to facilitate optimal protein-protein binding and/or reduce nonspecific or background interactions. Reagents that improve the efficiency of the assay, such as protease inhibitors, nuclease inhibitors, antimicrobial agents, etc., may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 10 hours will be sufficient.

A compound can affect LFG by either stimulating or inhibiting LFG. For example, a compound "inhibits" LFG if the cell is more sensitive to Fas-mediated apoptosis. A compound "stimulates" LFG if the cell is less sensitive to Fas-mediated apoptosis.

The sample containing LFG can be any sample of interest. The sample may be a cell sample or a membrane sample prepared from a cell sample. Any cell expressing LFG can be used in the method of the invention. For example, cell lines or primary cells expressing lifeguard (LFG) polypeptide can be used. Suitable cells also include any host cells containing a recombinant LFG vector of the invention; the host cells functionally express the LFG polypeptide. The effect of the compound on LFG can be measured by assessing apoptosis and the timing of a apoptotic response. Methods for assessing Fas mediated apoptosis are well known in the art. For example, a cell with an antibody that specifically binds Fas or the use of Fas ligand that specifically binds Fas, and any resulting apoptosis can be measured (T. Suda et al., Cell, 75, 1169, 1993). Specific, non-limiting assays to detect apoptosis include, but are not limited to agarose gel electrophoresis of low molecular weight isolated (to determine if a characteristic DNA laddering appears), in situ end labeling (ISEL), immunohistochemical analysis combined with ISEL, $^3$HdTr nuclear fragmentation assays, Annexin V binding, cell survival using MTT or derivatives thereof, cell survival assayed by crystal violet staining, and measurements of cell survival (e.g., Wood et al., Neuron 11:621–32, 1993; Wijsman et al., J. Histochem. Cytochem. 41:7–12, 1993; Matzinger, P., J. Immunol methods 145:185–192, 1991; Martin et al., J. Exp. Med. 182:1545, 1995, all herein incorporated by reference).

TREATMENT OF AN APOPTOSIS-ASSOCIATED DISORDER

The antibodies and polynucleotides of the invention can be used to detect or treat an apoptosis-associated disorder such as a disorder associated with Fas-mediated apoptosis. The term "disorder associated with Fas-mediated apoptosis" denotes any disorder (e.g., cell proliferative, viral, neurologic, neuropsychiatric, muscular, and immnunological disorders, amongst others) having a clinical appearance related to an alteration in Fas mediated apoptosis. These disorders may be understood to be caused by defects in other molecules known to participate in signaling pathways related to apoptosis, or may still have no known molecule correlate. For example, it may be that only some patients with a specific disorder have abnormalities in Fas-mediated apoptosis function, while others with an identical syndrome have normal Fas-mediated apoptosis (their syndrome presumably produced by other genetic factors).

"Apoptosis" refers to the process of programmed cell death. Apoptosis-associated genes (and polypeptides) are associated with the regulation (enhanced or decreased) of the apoptosis phenomena in a cell. Apoptosis as is known in the art is characterized by cell shrinkage, chromatin condensation, and DNA cleavage into nucleosomal fragments. An "apoptosis-regulating gene" ("apoptotic gene" or "apoptosis gene") means a gene which regulates (either enhances or inhibits) the process of apoptosis. "Apoptotic deficient" or "apoptotic defective" refers to the inability of an apoptosis-regulating gene or polypeptide to induce enhance or inhibit apoptosis, or cell death. "Wild-type apoptotic" means a polypeptide with at least 70% of the biological activity of an unaltered polypeptide associated with apoptosis, and preferably, the wild-type polypeptide has at least 90% of the biological activity of unaltered polypeptide.

Disorders susceptible to treatment by the method of the subject invention include those caused by excessive cell death due to viral infection. A specific, non-limiting example of such a disorder is an HIV infection which ultimately causes AIDS, and is characterized by the excessive dying of lymphatic T cells in the patient. Disorders susceptible to treatment by the method of the invention also include disorders related to excessive cell proliferation.

A "cell proliferative disorder" include any disorder associated with abnormal cell proliferation, such as various cancers, both malignant and benign. Degenerative disorders such as cystic fibrosis (CF) also can be treated by the modulation of the apoptotic pathway to change the balance of cell proliferation and cell death and alleviate the disease symptoms and/or progression. Immunologic disorders such as rheumatoid arthritis can also be treated by the modulation of the apoptotic pathway to change the balance of cell proliferation and death, and thus can be treated by a method of the invention. Additionally, neurodegenerative disorders resulting from apoptosis of neural cells can be treated.

The invention can be used to determine the prognosis of a disorder. It may also be useful in guiding choices between different treatment regimens in patients with disorder associated with Fas-mediated apoptosis or related disorders. The "prognosis" is a forecast as to the probable outcome of an attack of a disease; the prospect as to recovery from a disorder as indicated by the nature and symptoms of the case. In addition, the invention may be used to identify or treat individuals who are "at risk" of developing a disorder associated with Fas-mediated apoptosis. These individuals may be identified by a method of the invention for detecting the presence or absence of LFG or by any other diagnostic means, and/or may be treated by a method of the invention, prior to the actual onset of the clinical appearance of disorder. The "clinical appearance" can be any sign or symptom of the disorder.

Essentially, any disorder which is etiologically linked to altered expression of LFG or an allele of LFG could be considered susceptible to treatment with LFG. For example, in a disease associated with increased LFG expression could be treated with a reagent that inhibits the expression or function of LFG, and any disorder which is etiologically linked decreased expression or function of LFG could be treated with a reagent that augments the expression or function of LFG, including treatments with polynucleotides encoding LFG or the LFG polypeptide itself.

For purposes of the invention, an antibody or nucleic acid probe specific for LFG may be used to detect LFG polypeptide (using antibody) or polynucleotide (using nucleic acid probe) in subject samples such as biological fluids, cells, tissues; or nucleic acid. Any specimen containing a detectable amount of antigen or polynucleotide can be used. Examples of biological fluids of use with the invention are blood, serum, plasma, urine, mucous, and saliva. Tissue or cell samples can also be used with the subject invention. The samples can be obtained by many methods such as cellular aspiration, or by surgical removal of a biopsy sample.

The invention provides a method for detecting LFG, for example, which comprises contacting an LFG-specific antibody or nucleic acid probe with a cell suspected of expressing LFG and detecting binding to the antibody or nucleic acid probe. The antibody reactive with the LFG polypeptide or the nucleic acid probe that binds LFG under stringent conditions is preferably labeled with a compound which allows detection of binding to LFG. A preferred sample of this invention is blood, tissue or any sample from a subject affected a disorder associated with Fas mediated apoptosis.

The level of LFG in the subject cell can be compared with the level in a cell not affected by the disease process. The cell not affected by the disease process can be taken from the same subject, or can be from a control subject not affected by the disease process, or can be from a cell line. Preferably the subject is human.

When the cell component to be analyzed is nucleic acid, it may be necessary to amplify the nucleic acid prior to binding with the LFG specific probe. Preferably, polymerase chain reaction (PCR) is used, however, other nucleic acid amplification procedures such as ligase chain reaction (LCR), ligated activated transcription (LAT) and nucleic acid sequence-based amplification (NASBA) may be used.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The concentration of detectably labeled monoclonal antibody which is administered should be sufficient such that the binding to those cells having the polypeptide is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. Such dosages may vary, for example, depending on whether multiple injections are given, antigenic burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that deleterious radiation with respect to the host is minimized. Ideally, a radioisotope used for in vivo imaging will lack a particle emission, but produce a large number of photons in the 140–250 keV range, which may readily be detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bi-functional chelating agents such as diethylenetriamine-pentacetic acid (DTPA) and ethylenediarninetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies or polynucleotides of the invention can be used in vitro and in vivo to monitor the course of amelioration of a disorder associated with Fas-mediated apoptosis in a subject. Thus, for example, by measuring the increase or decrease in the number of cells expressing antigen comprising a LFG polypeptide of the invention or changes in the concentration of such antigen present on cells or in various body fluids, it would be possible to determine whether a particular therapeutic regimen aimed at ameliorating the disorder associated with Fas-mediated apoptosis is effective. The term "ameliorate" denotes a lessening of the detrimental effect of the disorder associated with Fas-mediated apoptosis in the subject receiving therapy.

The present invention identifies a polynucleotide sequence that can be expressed in an altered manner as compared to expression in a normal cell, therefore it is possible to design appropriate therapeutic or diagnostic techniques directed to this sequence. The antibodies and polynucleotides of the invention can be used to detect or to treat a disorder associated with Fas-mediated apoptosis. Detection of elevated levels of LFG expression is accomplished by hybridization of nucleic acids isolated from a cell of interest with a LFG polynucleotide of the invention. Analysis, such as Northern Blot analysis, are utilized to quantitate expression of the LFG. Other standard nucleic acid detection techniques will be known to those of skill in the art.

Treatment can include modulation of LFG gene expression and LFG activity by administration of a therapeutically effective amount of a reagent that modulates LFG. The term "modulate" envisions the suppression of expression of LFG when it is over-expressed, or augmentation of the expression of LFG when it is under-expressed. Where a disorder is associated with the decreased expression of LFG, nucleic acid sequences that encode LFG can be used. Where a disorder is associated with the increased expression of LFG, nucleic acid sequences that interfere with the expression of LFG can be used. This approach utilizes, for example, antisense nucleic acid, ribozymes, or triplex agents to block transcription or translation of LFG mRNA, either by masking that mRNA with an antisense nucleic acid or triplex agent, or by cleaving it with a ribozyme.

Antisense nucleic acids are DNA or RNA molecules that are complementary to at least a portion of a specific mRNA molecule (Weintraub, 1990, Scientific American, 262:40). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target LFG-producing cell. The use of antisense methods to inhibit the in vitro translation of genes is well known in the art (Marcus-Sakura, 1988, Anal.Biochem., 172:289).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., 1991, Antisense Res. and Dev., 1(3):227; Helene, C., 1991, Anticancer Drug Design, 6(6):569).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, 1988, J.Amer.Med. Assn., 260:3030). A major advantage of this approach is that, because they are sequence-specific, only mRNAs with particular sequences are inactivated.

There are two basic types of ribozymes namely, tetrahymena-type (Hasselhoff, 1988, Nature, 334:585) and "hammerhead"-type. Tetrahymena-type ribozymnes recognize sequences which are four bases in length, while "hammerhead"-type ribozyrnes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The present invention also provides gene therapy for the treatment of disorders associated with Fas-mediated apoptosis which are associated with altered amounts of LFG protein. Such therapy would achieve its therapeutic effect by introduction of a therapeutic polynucleotide into cells having the disorder. The "therapeutic polynucleotide" may be polynucleotide sequences encoding LFG, or antisense polynucleotide specific for LFG. Delivery of the therapeutic polynucleotide can be achieved using a recombinant expression vector such as a chimeric virus or a colloidal dispersion system. Especially preferred for therapeutic delivery of antisense sequences, or LFG polynucleotides, is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus or a lentiviral vector having human, feline, porcine or equine immunodeficiency virus sequences. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV), human immunodeficiency virus (HIV), feline immunodeficiency virus (FIV) or equine immunodeficiency virus (EIV). Preferably, when the subject is a human, a vector such as the gibbon ape leukemia virus (GaLV) or a lentivirus is utilized. A number of additional retroviral vectors can incorporate multiple genes. All of these vectors can transfer or incorporate a gene for a selectable marker so that transduced cells can be identified and generated. By inserting a LFG sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the LFG polynucleotide. LFG expression can be regulated, for example, spatially, temporally or both.

Another targeted delivery system for the therapeutic polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 $\mu$m can encapsulate a substantial percentage of an aqueous buffer containing large macromolecules. RNA, DNA and intact virions can be encapsulated within the aqueous interior and be delivered to cells in a biologically active form (Fraley et al.,1981, Trends Biochem. Sci., 6:77). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al.,1988, Biotechniques, 6:682).

The composition of the liposome is usually a combination of phospholipids, particularly high-phase-transition-temperature phospholipids, usually in combination-with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidyl-glycerols, where the lipid moiety contains from 14–18 carbon atoms, particularly from 16–18 carbon atoms, and is saturated. Illustrative phospholipids include egg phosphatidylcholine, dipalmitoylphosphatidylcholine and diste aroylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

This invention involves administering to a subject a therapeutically effective dose of a pharmaceutical composition containing the compounds of the present invention and a pharmaceutically acceptable carrier. "Administering" the pharmaceutical composition of the present invention may be accomplished by any means known to the skilled artisan. By "subject" is meant any mammal, preferably a human.

The pharmaceutical compositions are preferably prepared and administered in dose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention are in general administered topically, intravenously, orally or parenterally or as implants, but even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, 1990, Science, 249:1527–1533, which is incorporated herein by reference.

The pharmaceutical compositions according to the invention may be administered locally or systemically. By "therapeutically effective dose" is meant the quantity of a compound according to the invention necessary to prevent, to cure or at least partially arrest the symptoms of the disorder and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al., eds., 1990, Goodman And Gilman's: The Pharmacological Bases of Therapeutics, 8th ed., Pergamon Press; and Remington's Pharmaceutical Sciences, 1990, 17th ed., Mack Publishing Co., Easton, Pa., each of which is herein incorporated by reference.

Thus, the identification of LFG provides a useful tool for diagnosis, prognosis and therapeutic strategies associated with expression of LFG.

KITS

The materials for use in the assay of the invention are ideally suited for the preparation of a kit. Such a kit may comprise a carrier means containing one or more container means such as vials, tubes, and the like, each of the container means comprising one of the separate elements to be used in the method. One of the container means may comprise a probe which is or can be detectably labeled. Such probe may be an antibody or nucleic acid sequence specific for LFG, or specific fragments thereof. For example, oligonucleotide probes of the present invention can be included in a kit and used for examining the presence of LFG in a sample, as well as the quantitative (relative) degree of binding of the probe for determining the occurrence of specific strongly binding (hybridizing) sequences, thus indicating the likelihood for an subject having or predisposed to a disorder associated with LFG.

The kit may also contain a container comprising a reporter-means, such as a biotin-binding protein, such as avidin or streptavidin, bound to a reporter molecule, such as an enzymatic, fluorescent, or radionucleotide label to identify the detectably labeled oligonucleotide probe.

Where the kit utilizes nucleic acid hybridization to detect the target nucleic acid, the kit may also have containers containing nucleotide(s) for amplification of the target nucleic acid sequence. When it is desirable to amplify the LFG target sequence, this can be accomplished using oligonucleotide(s) that are primers for amplification. These oligonucleotide primers are based upon identification of the flanking regions contiguous with the target nucleotide sequence.

The kit may also contain a container containing antibodies which bind to LFG, or specific fragments thereof. Such antibodies can be used to distinguish the presence of LFG or the level of expression of LFG in a specimen. Where the kit utilizes antibodies to detect LFG, these antibodies may be directly labeled. The kit may also contain a container containing a reporter means, such as avidin or steptavin, bound to a reporter molecule such as an enzymatic, fluorescent, or radionucleotide label to identify the directly labeled antibody Alternatively, the kit can utilizes antibodies that bind LFG that are unlabeled. The kit may then also contain a container containing a second antibody which binds to the antibody specific for LFG. The second antibody can be directly labeled. The kit may also a container containing a reporter means, such as avidin or steptavin, bound to a reporter molecule such as an enzymatic, fluorescent, or radionucleotide label to identify the directly labeled second antibody.

TRANSGENIC ANIMALS

In another embodiment, the present invention relates to transgenic animals having cells that express LFG. Such transgenic animals represent a model system for the study of LFG and disorders related to Fas-mediated apoptosis, and the study of LFG-based therapeutics.

The term "animal" here denotes all mammalian species except human. It also includes an individual animal in all stages of development, including embryonic and fetal stages. Farm animals (pigs, goats, sheep, cows, horses, rabbits and the like), rodents (such as mice), and domestic pets (for example, cats and dogs) are included within the scope of the present invention.

A "transgenic" animal is any animal containing cells that bear genetic information received, directly or indirectly, by deliberate genetic manipulation at the subcellular level, such as by microinjection or infection with recombinant virus. "Transgenic" in the present context does not encompass classical crossbreeding or in vitro fertilization, but rather denotes animals in which one or more cells receive a recombinant DNA molecule. Although it is highly preferred that this molecule be integrated within the animal's chromosomes, the present invention also contemplates the use of extrachromosomally replicating DNA sequences, such as might be engineered into yeast artificial chromosomes.

The term "transgenic animal" also includes a "germ cell line" transgenic animal. A germ cell line transgenic animal is a transgenic animal in which the genetic information has been taken up and incorporated into a germ line cell, therefore conferring the ability to transfer the information to offspring. If such offspring in fact possess some or all of that information, then they, too, are transgenic animals.

It is highly preferred that the transgenic animals of the present invention be produced by introducing into single cell embryos DNA encoding LFG, in a manner such that the polynucleotides are stably integrated into the DNA of germ line cells of the mature animal and inherited in normal Mendelian fashion. Advances in technologies for embryo micromanipulation now permit introduction of heterologous DNA into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a preferred method, developing embryos are infected with a retrovirus containing the desired DNA, and transgenic animals produced from the infected embryo.

In a most preferred method the appropriate DNAs are coinjected into the pronucleus or cytoplasm of embryos, preferably at the single cell stage, and the embryos allowed to develop into mature transgenic animals. These techniques are well known. For instance, reviews of standard laboratory procedures for microinjection of heterologous DNAs into mammalian (mouse, pig, rabbit, sheep, goat, cow) fertilized ova include: Hogan et al., *Manipulating the Mouse Embryo* (Cold Spring Harbor Press 1986); Krimpenfort et al., 1991, *Bio/Technology* 9:86; Palmiter et al., 1985, *Cell* 41:343; Kraemer et al., *Genetic Manipulation of the Early Mammalian Embryo* (Cold Spring Harbor Laboratory Press 1985); Hammer et al., 1985, *Nature*, 315:680; Purcel et al., 1986, *Science*, 244:1281; Wagner et al., U.S. Pat. No. 5,175,385; Krimpenfort et al., U.S. Pat. No. 5,175,384, the respective contents of which are incorporated by reference.

The CDNA that encodes LFG can be fused in proper reading frame under the transcriptional and translational control of a vector to produce a genetic construct that is then amplified, for example, by preparation in a bacterial vector, according to conventional methods. See, for example, the standard work: Sambrook et al., *Molecular Cloning: a Laboratory Manual* (Cold Spring Harbor Press 1989), the contents of which are incorporated by reference. The amplified construct is thereafter excised from the vector and purified for use in producing transgenic animals.

The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. In addition, homologous recombination can be used to alter one or more amino acids of LFG to recapitulate a human disease state. As used herein, the term "transgenic" includes any transgenic technology familiar to those in the art which can produce an organism carrying an introduced transgene or one in which an endogenous gene has been rendered non-functional or knocked out.

The transgene to be used in the practice of the subject invention is a DNA sequence comprising a modified LFG coding sequence. In a preferred embodiment, the endogenous LFG gene is disrupted by homologous targeting in embryonic stem cells. For example, the entire murine LFG gene may be deleted. Optionally, the LFG disruption or deletion may be accompanied by insertion of or replacement with other DNA sequences, such as a non-functional LFG sequence. In other embodiments, the transgene comprises DNA antisense to the coding sequence for LFG. In another embodiment, the transgene comprises DNA encoding an antibody or receptor peptide sequence which is able to bind to LFG. Where appropriate, DNA sequences that encode proteins having LFG activity but differ in nucleic acid sequence due to the degeneracy of the genetic code may also be used herein, as may truncated forms, allelic variants and interspecies homologues.

EXAMPLES

The following examples are intended to illustrate but not to limit the invention in any manner, shape, or form, either explicitly or implicitly. While they are typical of those that might be used, other procedures, methodologies, or techniques known to those skilled in the art may alternatively be used.

Example 1

Cloning of LFG

A cDNA library was generated from a human lung fibroblast cell line, MRC-5 in a retroviral vector. This cell line is not sensitive to FasL but, like many other cell lines, is sensitive to the signal in the presence of the protein synthesis inhibitor cyclohexamide (Yonehara et al., *J. Exp. Med.*, 169, 1747, 1989). This suggests the existence of a labile protein and/or the need for new protein synthesis to protect from the Fas signal.

Retroviral vectors containing the cDNA library were generated and used to transduce HeLa cells. This cell line is sensitive to FasL, or agonist antibody in the absence of cyclohexamide. The transduced cells were maintained in the presence of a mouse anti-human Fas agonistic antibody (CH11) to induce apoptosis through a Fas mediated cell death signal. The rationale for the experiment is that a cell will survive this selection either due to the overexpression or the ectopic expression of a cDNA provided by the retrovirus vector. Genomic DNA was prepared from the surviving pool of cells (HeLa Fas$^R$ Pool) and used as a template to amplify cDNA inserts by polymerase chain reaction (PCR), using primers straddling the CDNA cloning site in the retroviral vector.

The most prominent PCR product was cloned and subjected to sequence analysis. Nucleotide sequencing of the cDNA clone revealed a long open reading frame encoding a protein of 316 amino acids with a calculated molecular weight of 34.6 kD (FIG. 1A). Sequence analysis of genomic and cDNA clones revealed the existence of an upstream stop codon in frame with the initiating methionine, suggesting that this is the full length protein. The nucleic acid sequence was named lifeguard (LFG) the function of this gene.

Homology search of the existing databases revealed that this protein, which was designated as LFG (for lifeguard) is the human homologue of a recently reported rat protein, neural membrane protein 35 (NMP35) (B. Schweitzer et al., *Mol. Cell Neurosci.*, 11, 260 1998). This latter protein was identified using differential display to find genes that are regulated during development of the rat sciatic nerve. Analyses were done to document the expression of LFG. Although expression of the LFG was noted to be high in neural tissues expression, it was not limited to just neuronal tissues.

Figure 1B:
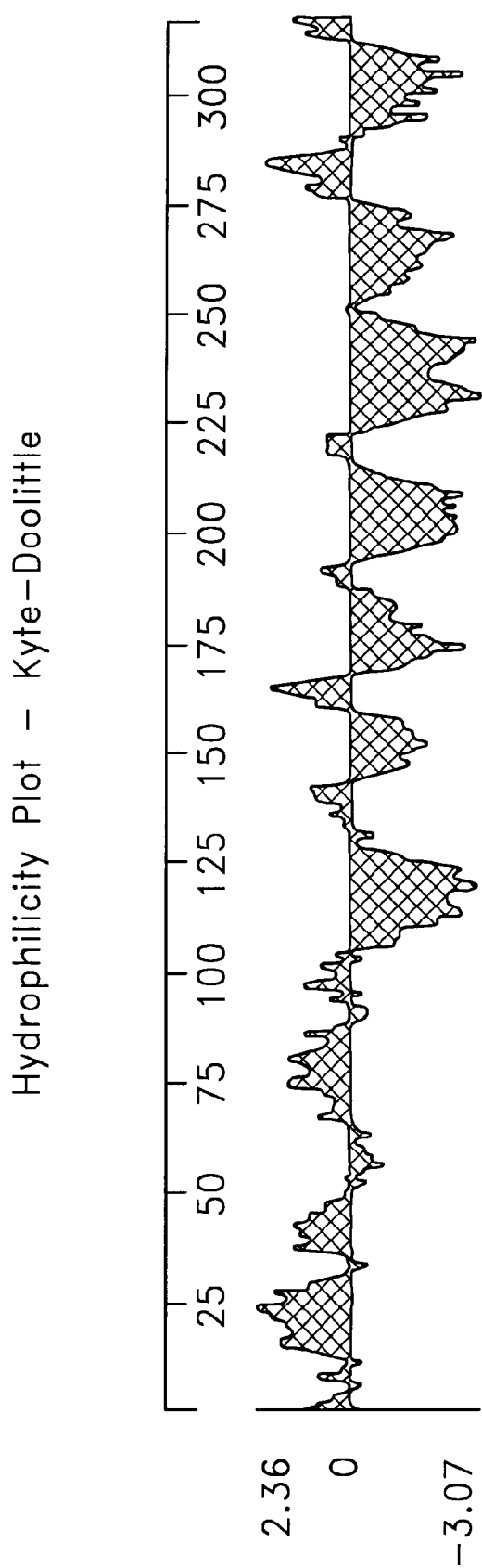
FIG. 1B is a Kyte-Doolittle hydrophilicity plot illustrating that LFG is predicted to be a seven membrane spanning protein. The prediction was done using the protean function of DNAS-TAR.

LFG has significant homology in its C-terminal half to a rat glutamate binding protein (K. N. Kumar et al., *Nature*, 354, 70, 1991), the drosophila NMDA receptor associated protein (A. Pellicena-Palle et al., *Biochim. Biophys. Acta*, 1261, 301,. 1995), and two C. elegans proteins of unknown function (FIG. 1A). Hydropathy plots predict that LFG is a seven membrane spanning protein (FIG. 1B). Indeed the pfam program assigned it to an uncharacterized protein family UPF005 whose members are predicted to contain seven membrane spanning domains and which share a signature in the region beginning with the third spanning domain and ending in the middle of the fourth (L. Walter et al., *Genomics*, 28, 301, 1995).

The chromosomal localization of the LFG gene was determined using a human/rodent somatic hybrid panel. The result showed that the LFG gene is localized on human chromosome 12. This was confirmed by fluorescence in situ hybridization and the subchromosomal revealed it to be on 12q13.

Example 2

Function of LFG

Figure 2A:
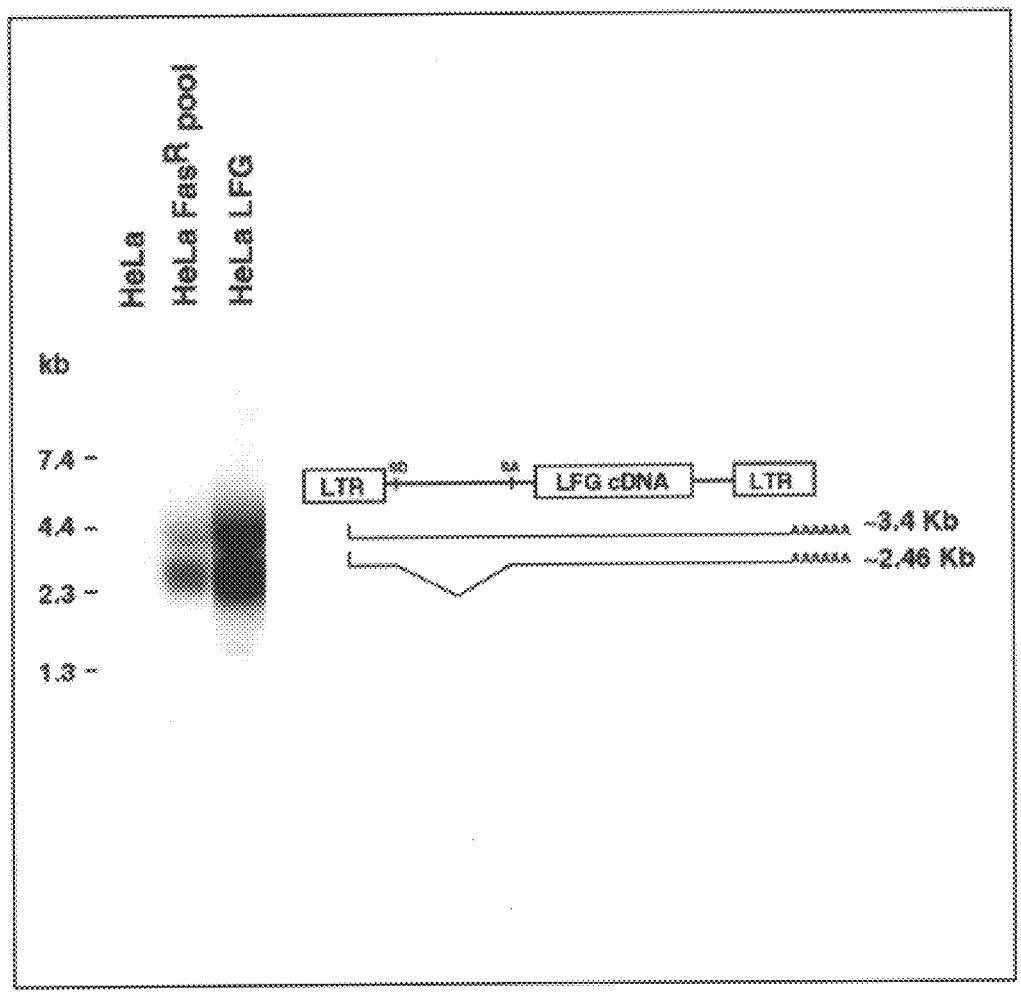
FIG. 2A is a diagram of the transcripts obtained from the LFG sequences.

To confirm the role of LFG in protecting from Fas induced apoptosis, HeLa cells were transduced with a retroviral vector containing LFG cDNA and treated with the CH11 antibody. Northern blot analysis of RNA from transduced cells show the expression of LFG, whereas expression was not observed in untransduced cells. LFG expression was also detected in the HeLa Fas$^R$ pool. FIG. 2A shows cell survival after treatment with the CH11 agonistic antibody HeLa cells have 17% cell survival 72 hr after treatment, whereas the Fas$^R$ pool, and HeLa cells infected with the LFG vector exhibit survival of 102% and 83% respectively.

Figure 2B:
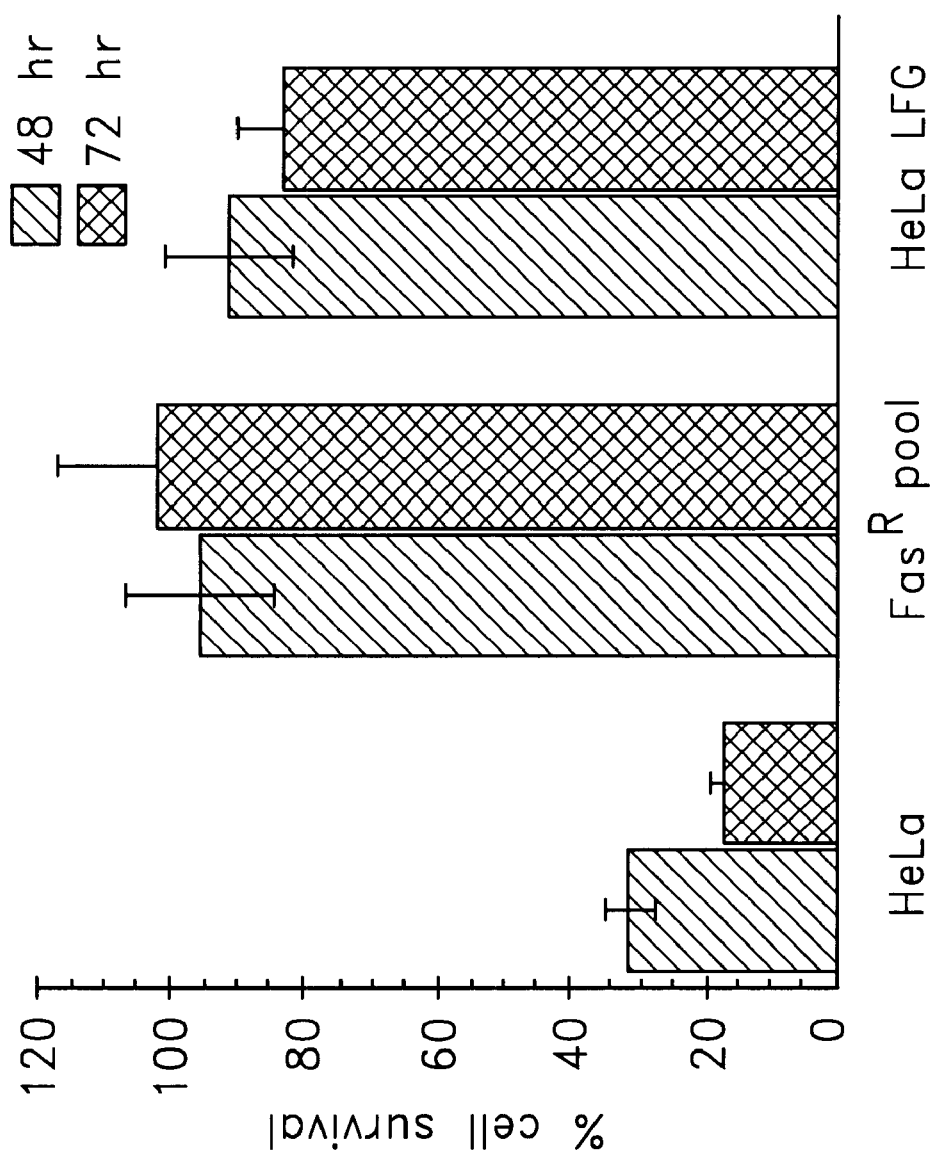
FIG. 2B is a bar graph demonstrating that LFG protects cells from Fas mediated apoptosis. The indicated cell lines were challenged with mouse anti-human Fas antibody (CH11) and surviving cells monitored 48 hr and 72 hr later. Percent cell survival is expressed relative to cells that were not treated with anti-Fas antibody (mean ±S.D.; n=3).
Figure 2C:
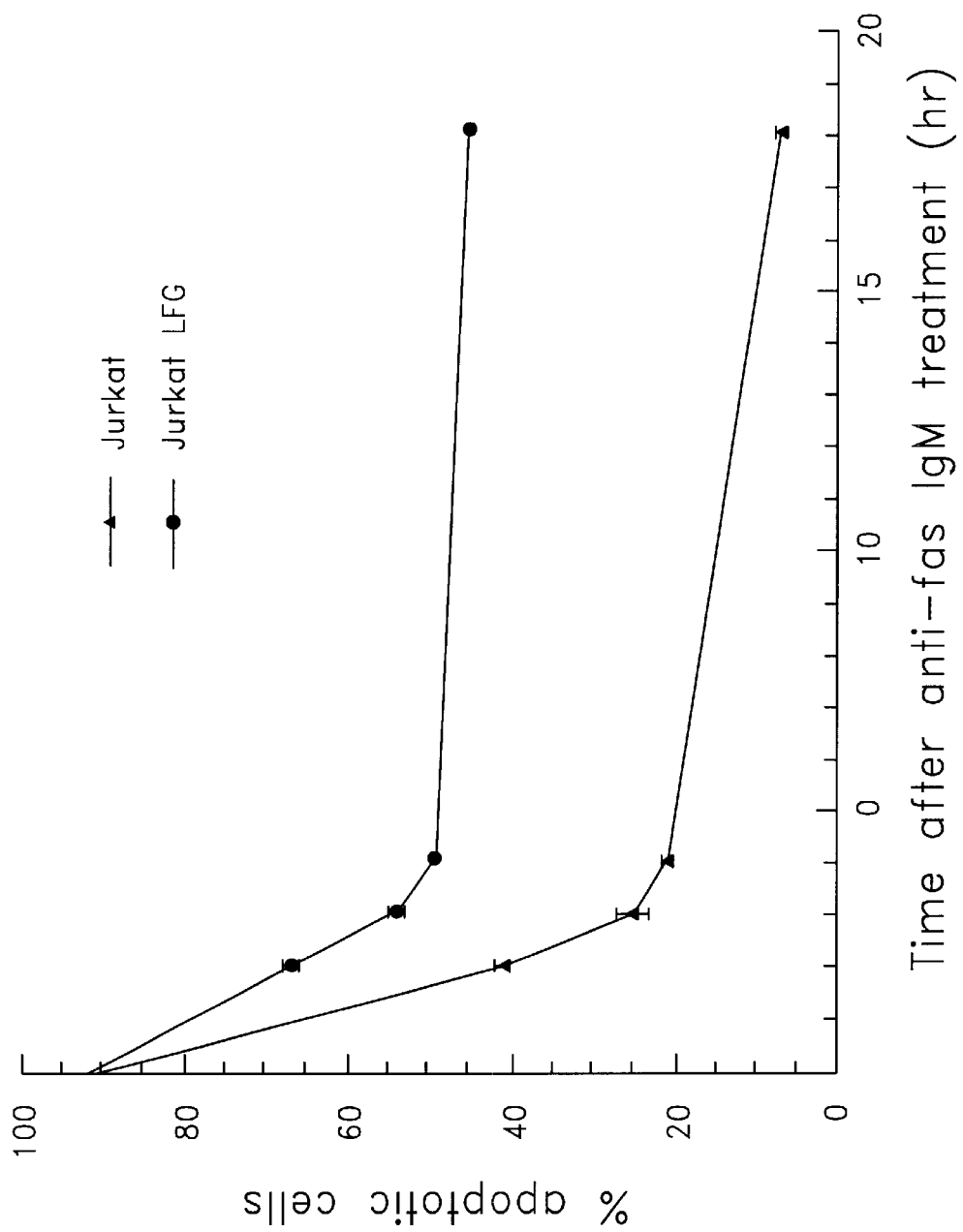
FIG. 2C is a bar graph showing the survival of Jurkat cells (human T-cell line) and Jurkat cells transduced with a LFG retroviral vector. The cells were challenged with CH11 antibody, and annexin V expression on the cell surface was measured over time (Martin et al., *J. Exp. Med.*, 182, 1545, 1995). Cell survival is plotted as a percentage of untreated cells.

Furthermore, LFG can protect another cell type, a human Jurkat T-cell line, from Fas mediated apoptosis. This cell lines is exquisitely sensitive to the Fas signal. No LFG transcripts were detected in Jurkat cells by Northern blot analysis. These cells were infected with LFG retroviral vectors, treated with CH11, and death monitored using annexin V as an early index of apoptosis (Martin et al., *J. Exp. Med.*, 182, 1545, 1995). As shown in FIG. 2B, about 50% of the cells infected with LFG retroviral vectors were annexin V negative 20h after treatment with CH11, and hence have not initiated apoptosis. Cells transduced with a retroviral vector with LFG in the antisense orientation behaved as untransduced cells.

Figure 2D:
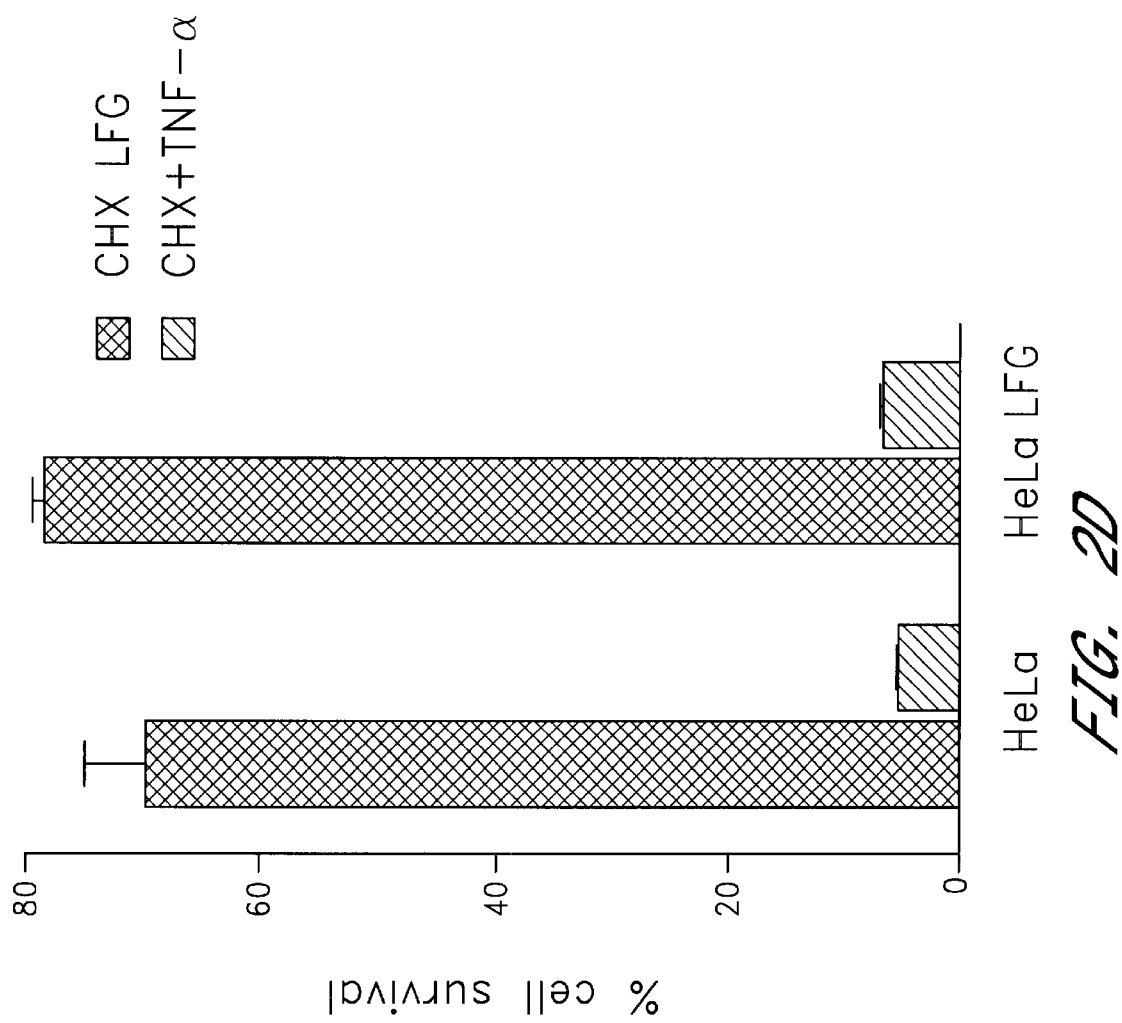
FIG. 2D is a bar graph demonstrating that LFG does not protect from TNF- mediated apoptosis. HeLa cells, and those expressing LFG were treated with cyclohexamide (CHX) or TNF- and CHX and cell survival was measured 24 hr later. Percentage cell survival is expressed relative to untreated cells (mean ±S.D.; n=3).

To determine whether LFG also protects from TNF-mediated apoptosis, HeLa cells, and HeLa cells expressing LFG transcripts were treated with TNF-and cyclohexamide. The results showed that LFG did not affect the TNF-mediated death signal (FIG. 2D). This sensitivity is also observed for WEHI-13VAR (K. S. Khabar et al., *Immunol. Lett.*, 46, 107, 1995) cells that are sensitive to TNF-alone. Furthermore, protection was not afforded by LFG expression to cell death mediated by the TNF-related apoptosis-inducing ligand, TRAIL (S. R. Wiley et al., *Immunity*, 3, 673, 1995) or the broad spectrum protein kinase inhibitor staurosporine (data not shown).

Example 3

Expression of LFG

The tissue distribution of the LFG transcripts in various human tissues were examined by Northern blot analysis. LFG is expressed in most tissues (e.g., heart, brain, liver, pancreas, lung, muscle, uterus, bladder, kidney, cervix, ovary, testis, prostate, amongst others) except spleen and placenta. Two major LFG transcripts of 1.3 kb and 4.4 Kb were detected.

Further analysis has revealed that the 1.3 Kb signal is generated by two transcripts, close in size, that are generated by utilizing an alternative polyadenlyation signal but which code for the same protein product. Similarly, sequence analysis of overlapping cDNA clones that constitute the 4.4 Kb transcripts revealed an identical coding sequence to the 1.3 Kb transcripts, with a large 5' untranslated region.

The expression levels of LFG were extremely high in the brain. Dissection of the regions of the brain show that the expression is distributed in all the areas examined (frontal lobe, temporal lobe, hippocampus, amygdala, paracentral gyrus, portcentral gyrus, and occipital lobe). In situ hybridization analysis of mouse brain sections revealed LFG is expressed mostly in neurons and the highest expression was observed in the hippocampus (D. M. Simmons et al., *J. Histotech*, 12, 169, 1989). Within the hippocampus, LFG expression is also differential with highest expression in CA3, compared to CA2 and CA1 (on average 36 silver grains over CA3 pyramidal cells versus 26 grains over CA1 pyramidal cells). No cells exhibiting glial cell morphology (cell body profile under 6 um when nucleus was visible with large amounts of condensed chromatin at nuclear membrane) expressed LFG as assayed by significant silver grain deposition over these nuclei.

Example 4

Cellular Localization of LFG

To determine the cellular localization of LFG, HeLa cells were transiently transfected with an amino-terminal myc epitope-tagged LFG (myc-LFG) expression vector. Confocal microscopy revealed LFG to be cytoplasmic, and predominantly membrane associated, with peri-nuclear staining reminiscent of endoplasmic reticulum and Golgi structures and distribution in vesicles and at the cell membrane. Biochemical fractionation of 293 cells transfected with expression vectors for myc-LFG or human Fas confirms that LFG is membrane associated.

The interaction of LFG with components of the Fas signaling pathway was investigated. Fas and LFG can be co-immunoprecipitated following transient transfection. Immunoprecipitation and immunoblot analysis revealed that anti-human Fas antibodies can co-immunoprecipitate myc-LFG, whereas no myc-LFG precipitated with anti-human FADD antibodies. These results suggest that LFG is associated with Fas and inhibits FasL induced apoptosis, either by preventing formation of a death signaling complex, or by signaling for the induction of protecting molecules that prevent the transduction of the death signal.

Thus, a cDNA that uniquely protects from Fas mediated cell death has been cloned. The mechanism of Fas mediated apoptosis has been elucidated as recruitment of FADD to ligated Fas receptor and subsequent activation of caspase-8. In contrast apoptosis mediated by ligated TNF- receptor involves the ordered recruitment of TRADD, FADD and caspase-8 (A. Ashkenazi et al., *Science*, 281, 1305, 1998). The difference between the two, the adapter molecule TRADD, and the inability of LFG to protect from TNF-mediated death, therefore places the action of LFG upstream of FADD, at Fas or at the level of the Fas/FADD complex. In this respect an association between LFG and Fas has been demonstrated.

A number of cellular molecules have been identified that act on various components of the death signaling pathways. These include a soluble form of Fas (J. Cheng et al., *Science*, 263, 1759, 1994) and a secreted decoy receptor that binds to FasL and competes for ligand binding to Fas (R. M. Pitti et al., *Nature*, 369, 699, 1998). A group of proteins called FLIPs, that possess a DED, compete for the recruitment of FADD and caspase-8 at ligated receptors (J. Tschopp et al., *Curr. Opin. Immunol.*, 10, 552–8, 1998). An extension to this control is the molecule toso (Y Hitoshi et al., *Immunity*, 8, 461–71, 1998 that induces c-FLIP expression uniquely in hematopoietic lineages. Finally a number of molecules have been identified called inhibitors of apoptosis proteins (IAPs) (Q.L. Deveraux et al., *Embo. J.*, 2215–23, 1998) which inhibit caspase activity. Apart from the receptor/ligand mimics these molecules inhibit the signal pathway downstream of the receptor, and hence will inhibit the "death signal" from several receptors i.e. Fas and TNF- receptor. In contrast LFG seems to act very specifically on Fas.

Fas has been mainly characterized in the immune system and liver, and is primarily involved in regulating the immune response (S. Nagata et al., *Cell*, 88, 355, 1997) and the homeostasis of liver cell number (M. Adachi et al., *Nat. Genet.*, 11, 294, 1995). However expression of Fas and FasL are detectable in other tissues for example in the central nervous system in normal (C. Park et al., *Biochem. Biophys. Res. Commun.*, 252, 623, 1998), and brains suffering neurodegeneration (S. M. de la Monte et al., *J. Neurol. Sci.*, 152, 73, 1997). This suggests that Fas and FasL play a role in neurological diseases. The high expression of LFG found in the brain raises the possibility that LFG ordinarily protects from Fas-mediated neural cell death, especially in the hippocampus. In this regard the most proximal inhibitor molecules in the pathway, cFLIPS are not expressed in the brain (H. B. Shu et al., *Immunity*, 6, 751, 1997; S. Hu et al., *J. Biol. Chem.*, 272, 17255, 1997; S. M. Srinivasula et al., *J. Biol. Chem.*, 272, 18542, 1997; M. Irmler et al., *Nature*, 388, 190, 1997). Pathologies implicated to involve chromosome 12q13 that may have apoptosis as a component include leukemia (J. Dierlamm et al., *Genes Chromosomes Cancer*, 20, 155, 1997), lipomas (S. Merscher et al., *Genomics*, 46, 70, 1997); S. Knuutila et al., *Am. J. Pathol.*, 152, 1107, 1998) and Alzheimer's disease (Knuutila, supra, 1998).

The expression of LFG is not restricted to the brain but is seen in other tissues. Interestingly, studies have identified situations where both Fas and FasL are expressed on the same cells or in the same tissue without ensuing 'suicide' or 'fratricide'. It has been shown that a number of tumor cells are resistant to Fas mediated apoptosis and may even express both the Fas and FasL. In these situations, expression of LFG may in some part explain the survival of these cells.

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. An isolated polynucleotide encoding an amino acid sequence as set forth in SEQ ID NO:2.

2. An isolated polynucleotide selected from the group consisting of:
   (a) SEQ ID NO:1 where T can also be a U;
   (b) SEQ ID NO:1; and
   (c) Nucleic acid sequences complementary to SEQ ID NO:1.

3. The polynucleotide of claim 1, wherein said polynucleotide is operatively linked to an expression control sequence.

4. The polynucleotide of claim 3, wherein the expression control sequence is a promoter.

5. The polynucleotide of claim 4, wherein the promoter is tissue specific.

6. An expression vector containing a polynucleotide of claim 1.

7. The vector of claim 6, wherein the vector is a plasmid.

8. The vector of claim 6, wherein the vector is a viral vector.

9. The vector of claim 8, wherein the viral vector is a retroviral vector.

10. A host cell containing the vector of claim 6.

11. The host cell of claim 10, wherein the cell is a eukaryotic cell.

12. The host cell of claim 10, wherein the cell is a prokaryotic cell.

13. An isolated polypeptide comprising the amino acid sequence of SEQ ID NO:2.

* * * * *

SEQUENCE LISTING

```
<160> NUMBER OF SEQ ID NOS: 6

<210> SEQ ID NO 1
<211> LENGTH: 951
<212> TYPE: DNA
```

-continued

```
<213> ORGANISM: Homo Sapiens
<220> FEATURE:
<221> NAME/KEY: CDS
<222> LOCATION: (1)...(951)

<400> SEQUENCE: 1
```

| | | | | | | | | | | | | | | | | |
|---|---|---|---|---|---|---|---|---|---|---|---|---|---|---|---|---|
| atg | acc | cgg | gga | aag | ctc | tcc | gtg | gct | aac | aag | gcc | cct | ggg | acc | gag | 48 |
| Met | Thr | Arg | Gly | Lys | Leu | Ser | Val | Ala | Asn | Lys | Ala | Pro | Gly | Thr | Glu | |
| 1 | | | | 5 | | | | | 10 | | | | | 15 | | |
| ggg | cag | cag | cag | gtg | cat | ggc | gag | aag | aag | gag | gct | cca | gca | gtg | ccc | 96 |
| Gly | Gln | Gln | Gln | Val | His | Gly | Glu | Lys | Lys | Glu | Ala | Pro | Ala | Val | Pro | |
| | | 20 | | | | | 25 | | | | | 30 | | | | |
| tca | gcc | cca | ccc | tcc | tat | gag | gaa | gcc | acc | tct | ggg | gag | ggg | atg | aag | 144 |
| Ser | Ala | Pro | Pro | Ser | Tyr | Glu | Glu | Ala | Thr | Ser | Gly | Glu | Gly | Met | Lys | |
| | | 35 | | | | | 40 | | | | | 45 | | | | |
| gca | ggg | gcc | ttc | ccc | cca | gcc | ccc | aca | gcg | gtg | cct | ctc | cac | cct | agc | 192 |
| Ala | Gly | Ala | Phe | Pro | Pro | Ala | Pro | Thr | Ala | Val | Pro | Leu | His | Pro | Ser | |
| | 50 | | | | | 55 | | | | | 60 | | | | | |
| tgg | gcc | tat | gtg | gac | ccc | agc | agc | agc | tcc | agc | tat | gac | aac | ggt | ttc | 240 |
| Trp | Ala | Tyr | Val | Asp | Pro | Ser | Ser | Ser | Ser | Ser | Tyr | Asp | Asn | Gly | Phe | |
| 65 | | | | | 70 | | | | | 75 | | | | | 80 | |
| cca | ccg | gag | acc | atg | agc | tct | tca | cca | ctt | tca | gct | ggg | atg | acc | aag | 288 |
| Pro | Pro | Glu | Thr | Met | Ser | Ser | Ser | Pro | Leu | Ser | Ala | Gly | Met | Thr | Lys | |
| | | | | 85 | | | | | 90 | | | | | 95 | | |
| aaa | gtt | cgt | cga | gtc | ttt | gtc | aga | aag | gtc | tac | acc | atc | ctg | ctg | att | 336 |
| Lys | Val | Arg | Arg | Val | Phe | Val | Arg | Lys | Val | Tyr | Thr | Ile | Leu | Leu | Ile | |
| | | | 100 | | | | | 105 | | | | | 110 | | | |
| caa | ctg | ctg | gtg | acc | ttg | gct | gtc | gtg | gct | ctc | ttt | act | ttc | tgt | gac | 384 |
| Gln | Leu | Leu | Val | Thr | Leu | Ala | Val | Val | Ala | Leu | Phe | Thr | Phe | Cys | Asp | |
| | | 115 | | | | | 120 | | | | | 125 | | | | |
| cct | tgt | caa | gga | cta | tgt | tca | ggc | caa | cca | ggc | tgg | tac | tgg | gca | tcc | 432 |
| Pro | Cys | Gln | Gly | Leu | Cys | Ser | Gly | Gln | Pro | Gly | Trp | Tyr | Trp | Ala | Ser | |
| | 130 | | | | | 135 | | | | | 140 | | | | | |
| tat | gct | gtg | ttc | ttt | gca | acc | tac | ctg | acc | ctg | gct | tgc | tgt | tct | gga | 480 |
| Tyr | Ala | Val | Phe | Phe | Ala | Thr | Tyr | Leu | Thr | Leu | Ala | Cys | Cys | Ser | Gly | |
| 145 | | | | | 150 | | | | | 155 | | | | | 160 | |
| ccc | agg | agg | cat | ttc | ccc | tgg | aac | ctg | att | ctc | ctg | acc | gtc | ttt | acc | 528 |
| Pro | Arg | Arg | His | Phe | Pro | Trp | Asn | Leu | Ile | Leu | Leu | Thr | Val | Phe | Thr | |
| | | | | 165 | | | | | 170 | | | | | 175 | | |
| ctg | tcc | atg | gcc | tac | ctc | act | ggg | atg | ctg | tcc | agc | tac | tac | aac | acc | 576 |
| Leu | Ser | Met | Ala | Tyr | Leu | Thr | Gly | Met | Leu | Ser | Ser | Tyr | Tyr | Asn | Thr | |
| | | | 180 | | | | | 185 | | | | | 190 | | | |
| acc | tcc | gtg | ctg | ctg | tgc | ctg | ggc | atc | acg | gcc | ctt | gtc | tgc | ctc | tca | 624 |
| Thr | Ser | Val | Leu | Leu | Cys | Leu | Gly | Ile | Thr | Ala | Leu | Val | Cys | Leu | Ser | |
| | | 195 | | | | | 200 | | | | | 205 | | | | |
| gtc | acc | gtc | ttc | agc | ttc | cag | acc | aag | ttc | gac | ttc | acc | tcc | tgc | cag | 672 |
| Val | Thr | Val | Phe | Ser | Phe | Gln | Thr | Lys | Phe | Asp | Phe | Thr | Ser | Cys | Gln | |
| | 210 | | | | | 215 | | | | | 220 | | | | | |
| ggc | gtg | ctc | ttc | gtg | ctt | ctc | atg | act | ctt | ttc | ttc | agc | gga | ctc | atc | 720 |
| Gly | Val | Leu | Phe | Val | Leu | Leu | Met | Thr | Leu | Phe | Phe | Ser | Gly | Leu | Ile | |
| 225 | | | | | 230 | | | | | 235 | | | | | 240 | |
| ctg | gcc | atc | ctc | cta | ccc | ttc | caa | tat | gtg | ccc | tgg | ctc | cat | gca | gtt | 768 |
| Leu | Ala | Ile | Leu | Leu | Pro | Phe | Gln | Tyr | Val | Pro | Trp | Leu | His | Ala | Val | |
| | | | | 245 | | | | | 250 | | | | | 255 | | |
| tat | gca | gca | ctg | gga | gcg | ggt | gta | ttt | aca | ttg | ttc | ctg | gca | ctt | gac | 816 |
| Tyr | Ala | Ala | Leu | Gly | Ala | Gly | Val | Phe | Thr | Leu | Phe | Leu | Ala | Leu | Asp | |
| | | | 260 | | | | | 265 | | | | | 270 | | | |
| acc | cag | ttg | ctg | atg | ggt | aac | cga | cgc | cac | tcg | ctg | agc | cct | gag | gag | 864 |
| Thr | Gln | Leu | Leu | Met | Gly | Asn | Arg | Arg | His | Ser | Leu | Ser | Pro | Glu | Glu | |
| | | 275 | | | | | 280 | | | | | 285 | | | | |

```
tat att ttt gga gcc ctc aac att tac cta gac atc atc tat atc ttc    912
Tyr Ile Phe Gly Ala Leu Asn Ile Tyr Leu Asp Ile Ile Tyr Ile Phe
            290                 295                 300 acc ttc ttc ctg cag ctt ttt ggc act aac cga gaa tga                951
Thr Phe Phe Leu Gln Leu Phe Gly Thr Asn Arg Glu  *
305                 310                 315
```

<210> SEQ ID NO 2
<211> LENGTH: 316
<212> TYPE: PRT
<213> ORGANISM: Homo Sapiens

<400> SEQUENCE: 2

```
Met Thr Arg Gly Lys Leu Ser Val Ala Asn Lys Ala Pro Gly Thr Glu
 1               5                  10                  15

Gly Gln Gln Gln Val His Gly Glu Lys Lys Glu Ala Pro Ala Val Pro
            20                  25                  30

Ser Ala Pro Pro Ser Tyr Glu Ala Thr Ser Gly Glu Gly Met Lys
        35                  40                  45

Ala Gly Ala Phe Pro Pro Ala Pro Thr Ala Val Pro Leu His Pro Ser
    50                  55                  60

Trp Ala Tyr Val Asp Pro Ser Ser Ser Ser Tyr Asp Asn Gly Phe
65                  70                  75                  80

Pro Pro Glu Thr Met Ser Ser Pro Leu Ser Ala Gly Met Thr Lys
                85                  90                  95

Lys Val Arg Arg Val Phe Val Arg Lys Val Tyr Thr Ile Leu Leu Ile
            100                 105                 110

Gln Leu Leu Val Thr Leu Ala Val Val Ala Leu Phe Thr Phe Cys Asp
        115                 120                 125

Pro Cys Gln Gly Leu Cys Ser Gly Gln Pro Gly Trp Tyr Trp Ala Ser
    130                 135                 140

Tyr Ala Val Phe Phe Ala Thr Tyr Leu Thr Leu Ala Cys Cys Ser Gly
145                 150                 155                 160

Pro Arg Arg His Phe Pro Trp Asn Leu Ile Leu Leu Thr Val Phe Thr
                165                 170                 175

Leu Ser Met Ala Tyr Leu Thr Gly Met Leu Ser Ser Tyr Tyr Asn Thr
            180                 185                 190

Thr Ser Val Leu Leu Cys Leu Gly Ile Thr Ala Leu Val Cys Leu Ser
        195                 200                 205

Val Thr Val Phe Ser Phe Gln Thr Lys Phe Asp Phe Thr Ser Cys Gln
    210                 215                 220

Gly Val Leu Phe Val Leu Leu Met Thr Leu Phe Phe Ser Gly Leu Ile
225                 230                 235                 240

Leu Ala Ile Leu Leu Pro Phe Gln Tyr Val Pro Trp Leu His Ala Val
                245                 250                 255

Tyr Ala Ala Leu Gly Ala Gly Val Phe Thr Leu Phe Leu Ala Leu Asp
            260                 265                 270

Thr Gln Leu Leu Met Gly Asn Arg Arg His Ser Leu Ser Pro Glu Glu
        275                 280                 285

Tyr Ile Phe Gly Ala Leu Asn Ile Tyr Leu Asp Ile Ile Tyr Ile Phe
    290                 295                 300

Thr Phe Phe Leu Gln Leu Phe Gly Thr Asn Arg Glu
305                 310                 315
```

<210> SEQ ID NO 3
<211> LENGTH: 217

```
<212> TYPE: PRT
<213> ORGANISM: Rattus

<400> SEQUENCE: 3

Lys Ser Ile Arg Gln Ala Phe Ile Arg Lys Val Phe Leu Val Leu Thr
  1               5                  10                  15

Leu Gln Leu Ser Val Thr Leu Ser Thr Val Ala Ile Phe Thr Phe Val
             20                  25                  30

Gly Glu Val Lys Gly Phe Val Arg Ala Asn Val Trp Thr Tyr Tyr Val
         35                  40                  45

Ser Tyr Ala Ile Phe Phe Ile Ser Leu Ile Val Leu Ser Cys Cys Gly
 50                  55                  60

Asp Phe Arg Lys Lys His Pro Trp Asn Leu Val Ala Leu Ser Ile Leu
 65                  70                  75                  80

Thr Ile Ser Leu Ser Tyr Met Val Gly Met Ile Ala Ser Phe Tyr Asn
                 85                  90                  95

Thr Glu Ala Val Ile Met Ala Val Gly Ile Thr Thr Ala Val Cys Phe
            100                 105                 110

Thr Val Val Ile Phe Ser Met Gln Thr Arg Tyr Asp Phe Thr Ser Cys
            115                 120                 125

Met Gly Val Leu Leu Val Ser Val Val Leu Phe Ile Phe Ala Ile
130                 135                 140

Leu Cys Ile Phe Ile Arg Asn Arg Ile Leu Glu Ile Val Tyr Ala Ser
145                 150                 155                 160

Leu Gly Ala Leu Leu Phe Thr Cys Phe Leu Ala Val Asp Thr Gln Leu
                165                 170                 175

Leu Leu Gly Asn Lys Gln Leu Ser Leu Ser Pro Glu Glu Tyr Val Phe
            180                 185                 190

Ala Ala Leu Asn Leu Tyr Thr Asp Ile Ile Asn Ile Phe Leu Tyr Ile
            195                 200                 205

Leu Thr Ile Ile Gly Arg Ser Gln Gly
        210                 215

<210> SEQ ID NO 4
<211> LENGTH: 220
<212> TYPE: PRT
<213> ORGANISM: C. elegans

<400> SEQUENCE: 4

Gln Thr Val Arg Ala Ala Phe Val Arg Lys Val Phe Met Leu Val Thr
  1               5                  10                  15

Ile Met Phe Ala Ile Thr Ala Ala Phe Cys Val Ile Pro Met Val Ser
             20                  25                  30

Glu Pro Phe Gln Asp Trp Val Lys Asn Asn Phe Trp Val Tyr Phe Ile
         35                  40                  45

Ala Ile Ile Val Phe Leu Val Val Ala Ile Ala Leu Ser Cys Cys Gly
 50                  55                  60

Asn Leu Arg Arg Gln Phe Pro Val Asn Ile Ile Leu Leu Thr Ile Phe
 65                  70                  75                  80

Thr Leu Ser Ala Ala Val Met Thr Met Phe Val Thr Ala Cys Tyr Asn
                 85                  90                  95

Val Gln Ser Val Leu Ile Cys Leu Cys Ile Thr Thr Val Cys Ser Gly
            100                 105                 110

Ser Val Ile Ile Phe Ser Met Lys Thr Lys Ser Asp Leu Thr Ser Lys
            115                 120                 125
```

```
Met Gly Ile Ala Phe Met Leu Ser Met Val Leu Phe Ser Phe Gly Ile
        130                 135                 140

Phe Ala Leu Ile Phe Thr Leu Ala Pro Asn Trp Gln Phe Leu Tyr Ser
145                 150                 155                 160

Val Tyr Ser Gly Leu Ala Ala Leu Leu Met Met Phe Tyr Leu Ala Ile
                165                 170                 175

Asp Val Gln Leu Leu Met Gly Gly Arg Lys Tyr Glu Leu Ser Pro Glu
            180                 185                 190

Asp Tyr Ile Phe Ala Ala Met Glu Ile Phe Leu Asp Ile Leu Asn Ile
                195                 200                 205

Phe Leu Met Leu Leu Asn Ile Phe Gly Arg Gly Arg
        210                 215                 220

<210> SEQ ID NO 5
<211> LENGTH: 219
<212> TYPE: PRT
<213> ORGANISM: C. elegans

<400> SEQUENCE: 5

Lys Thr Val Arg Ala Ala Glu Val Arg Lys Val Glu Ser Leu Val Phe
1               5                   10                  15

Ile Met Leu Cys Ile Val Ala Ala Val Thr Val Ile Pro Trp Val His
                20                  25                  30

Asp Asp Thr Met Arg Met Val Arg Arg Asn Ser Ala Leu Tyr Leu Gly
            35                  40                  45

Ser Tyr Val Ile Phe Phe Val Thr Tyr Leu Ser Leu Val Cys Cys Glu
        50                  55                  60

Gly Val Arg Arg Lys Phe Pro Val Asn Leu Ile Val Thr Gly Ile Phe
65                  70                  75                  80

Thr Leu Ala Thr Ser Val Met Thr Met Val Ile Ser Ala His His Asp
                85                  90                  95

Ala Asn Val Val Leu Leu Ala Leu Ala Ile Cys Ile Gly Cys Thr Phe
            100                 105                 110

Ser Ile Val Ile Val Ala Ser Gln Thr Lys Phe Asp Leu Thr Ala His
        115                 120                 125

Met Gly Tyr Ile Leu Ile Ile Ser Met Cys Phe Met Phe Phe Gly Leu
    130                 135                 140

Val Val Val Ile Cys Ser Met Phe Phe Lys Ile Lys Phe Leu Met Met
145                 150                 155                 160

Val Tyr Ala Leu Gly Gly Ala Leu Ile Met Met Leu Tyr Leu Phe Leu
                165                 170                 175

Asp Val Gln Met Leu Met Gly Gly Lys Lys Tyr Glu Ile Ser Pro Glu
            180                 185                 190

Glu Tyr Ile Phe Ala Ser Val Gln Ile Phe Ile Asp Ile Val Gln Met
        195                 200                 205

Phe Trp Phe Leu Leu Ser Leu Phe Gly Ser Arg
    210                 215

<210> SEQ ID NO 6
<211> LENGTH: 203
<212> TYPE: PRT
<213> ORGANISM: Drosophila

<400> SEQUENCE: 6

Met Gly Gln Leu Ile Val Thr Phe Gly Ala Val Ala Leu Phe Val Tyr
1               5                   10                  15
```

-continued

```
His Glu Gly Thr Lys Thr Phe Ala Arg Asn Asn Met Trp Leu Phe Trp
            20              25              30

Val Ala Leu Gly Val Met Leu Val Thr Met Leu Ser Met Ala Cys Cys
            35              40              45

Glu Ser Val Arg Arg Gln Thr Pro Thr Asn Phe Ile Phe Leu Gly Leu
 50              55              60

Phe Thr Ala Ala Gln Ser Phe Leu Met Gly Val Ser Ala Thr Lys Tyr
 65              70              75              80

Ala Pro Lys Glu Val Leu Met Ala Val Gly Ile Thr Ala Ala Val Cys
            85              90              95

Leu Ala Leu Thr Ile Phe Ala Leu Gln Thr Lys Tyr Asp Phe Thr Met
           100             105             110

Met Gly Gly Ile Leu Ile Ala Cys Met Val Val Phe Leu Ile Phe Gly
           115             120             125

Ile Val Ala Ile Phe Val Lys Gly Lys Ile Ile Thr Leu Val Tyr Ala
           130             135             140

Ser Ile Gly Ala Leu Leu Phe Ser Val Tyr Leu Ile Tyr Asp Thr Gln
145             150             155             160

Leu Met Met Gly Gly Glu His Lys Tyr Ser Ile Ser Pro Glu Glu Tyr
            165             170             175

Ile Phe Ala Ala Leu Asn Leu Tyr Leu Asp Ile Ile Asn Ile Phe Met
            180             185             190

Tyr Ile Leu Thr Ile Ile Gly Ala Ser Arg Asp
            195             200
```